US005302530A

United States Patent [19]

Klein et al.

[11] Patent Number: 5,302,530

[45] Date of Patent: Apr. 12, 1994

[54] **DNA CODING FOR AN ANTIGEN OF *BLASTOMYCES DERMATITIDIS***

[75] Inventors: Bruce S. Klein; Laura H. Hogan; Jeffrey M. Jones, all of Madison, Wis.

[73] Assignee: Wisconsin Alumni Research Association, Madison, Wis.

[21] Appl. No.: 21,537

[22] Filed: Feb. 16, 1993

[51] Int. Cl.[5] .............................................. C12N 15/70

[52] U.S. Cl. ................................ 435/320.1; 536/23.7; 536/23.74

[58] Field of Search ................... 435/6, 320.1; 424/88; 536/23.5, 23.74; 530/350

[56] References Cited

U.S. PATENT DOCUMENTS 5,093,118 3/1992 Klein et al. .......................... 424/88

OTHER PUBLICATIONS

B. Klein et al., 85 J. Clin. Invest. 152-161 (1990) "Isolation, Purification, and Radiolabelling of a Novel 120-kD Surface Protein on *Blastomyces dermatitidi* Yeasts to Detect Antibody in Infected Patients".

R. Cox et al., 10 Infec. Immun. 42-47 (1974) "Isolation of Skin Test-Active Preparations from Yeast-Phase Cells of *Blastomyces dermatitudis*".

M. Lancaster; 13 Infec. Immun. 758-762 (1976) "Preparative Isotachophoretic Separation of Skin Test Antigens from Blastomycin Purified Derivative".

J. Green et al., 4 Curr. Microbiol. 293-296 (1980) "Isolation of an Antigen from *Blastomyces dermatitidis* That Is Specific for the Diagnosis of Blastomycosis".

K. Young et al., 33 Infec. Immun. 171-177 (1981) "Identification of the Active Precipitin Components in a Purified Preparation of the A Antigen of *Blastomyces dermatitidis*".

J. Jones, 30 Infec. Immun. 78-89 (1980) "Quantitation of Antibody Against Cell Wall Mannan and a Major Cytoplasmic Antigen of Candida in Rabbits, Mice, and Humans".

R. Greenfield, 101 J. Lab. Clin. Med. 758-771 (1983) "Quantitation of antibody to Candida mannan by enzyme-linked immunosorbent assay".

B. Klein et al., 314 H. Engl. J. Med. 529-534 (1986) "Isolation of *Blastomyces dermatitidis* in Soil Associated with a Large Outbreak of Blastomycosis in Wisconsin".

B. Klein et al., 133 Am. Rev. Respir. Dis. 144-148 (1986) "Comparison of the Enzyme Immunoassay, Immunodiffusion, and Complement Fixation Tests in Detecting Antibody in Human Sserum to the A Antigen of *Blastomyces dermatitidis*".

B. Klein et al., 155 J. Infec. Dis. 262-268 (1987) "Serological Tests for Blastomycosis: Assessments During a Large Point-Source Outbreak in Wisconsin".

B. Klein et al., 36 Am. Rev. Respir. Dis. 1333-1338 (1987) "Isolation of *Blastomyces dermatitidis* from Riverbank Soil and Evidence of its Transmission Along Waterways".

H. Towbin et al., 76 P.N.A.S. USA 4350-4354 (1979) "Electrophoretic transfer of proteins from polyacrylamide gels to nitrocellulose sheets: Procedure and some applications".

P. Minden et al., Handbook of Experimental Immunology, P. A. Davis Co., 463-492 (1967) "The Ammonium Sulphate Method to Measure Antigen-binding Capacity".

W. Fonzi et al., 5 Mol. Cell. Biol. 161-166 (1985) "Expression of the Gene for Ornithine Decarboxylas of *Saccharomyces cerevisiae* in *Escherichia coli*".

(List continued on next page.)

*Primary Examiner*—Margaret Parr
*Assistant Examiner*—Scott W. Houtteman
*Attorney, Agent, or Firm*—Quarles & Brady

[57] ABSTRACT

Disclosed herein is a c-DNA coding for an antigen of *B. dermatitidis*. The antigen can readily be expressed in quantity at high purity from the cDNA, and the antigen can then be used for assays for the disease. The unique sequence of the cDNA also permits the development of PCR primers so as to permit PCR assay techniques to be used in connection with this disease.

1 Claim, No Drawings

OTHER PUBLICATIONS

J. Badley et al., 6 Biotechniques 114–116 (1988) "A Simple, Rapid Method for the Purification of Poly A+ RNA".
J. Dover et al., 16 Nuc. Acids Res. 6127–45 (1988) "High efficiency transformation of *E. coli* by high voltage electroporation".
D. Holden et al., 8 EMBO J. 1927–34 (1989) "Mutation in a heat-regulated hsp70 gene of *Ustilago maydis*".
J. Donofrio et al., PCR Methods and Applications, 263–268, Cold Spring Harbor (1992) "Detection of Influenza A and B in Respiratory Secretions with the Polymerase Chain Reaction".
G. S. Deepe, Blastomycosis in Immunology of the Fungal Diseases, R. A. Cox, ed., CRC Press, Inc., Boca Raton, FL 139–164 (1989).
Bowman et al., Mol. Biol. Evol. 9(5):893–904. 1992.

DNA CODING FOR AN ANTIGEN OF *BLASTOMYCES DERMATITIDIS*

This invention was made with United States Government support awarded by the National Institute of Health (NIH), Grant Nos. AI-00905 and AI-31479. The United States Government has certain rights in this invention.

This invention relates to techniques for detecting the presence of a disease caused by *Blastomyces dermatitidis*. More particularly, it relates to a cDNA that codes for an antigen of a yeast that causes the disease.

BACKGROUND OF THE INVENTION

Blastomycosis is a disease that is caused by infection with the fungus *Blastomyces dermatitidis*. Humans and other animals (particularly dogs) are infected by inhaling aerosolized fungal spores from soil where the organism dwells. At body temperature, these spores convert to yeast forms. Acute primary pulmonary infection caused by the yeast can produce an influenza or pneumonia syndrome. Progressive forms of disease can cause serious damage.

The best available tests for this disease involve using antigens isolated from *B. dermatitidis* yeast in competitive binding RIA tests. See U.S. Pat. No. 5,093,118 (WI-1 protein); J. Green et al., 4 Curr. Microbiol. 293–96 (1980) ("A" antigen); and R. Cox et al., 10 Infect. Immun. 42–47 (1974) ("B-ASWS" antigen). The disclosures of these and all other articles and patents referred to herein are incorporated by reference as if fully set forth herein.

Existing supplies of B-ASWS antigen and A antigen are impure (see K. Young et al., 33 Infect Immun. 171–177 (1981); M. Lancaster et al., 13 Infect Immun. 758–762 (1976)), and they appear to be a mixture of cell wall components. It has not been possible to determine what portions of these two antigen are responsible for the antigenic response.

While WI-1 protein has now been isolated in reasonable purity, no one had previously been able to obtain DNA that would express this protein apart from *B. dermatitidis*. The amino acid sequence of WI-1 had not previously been determined and the cysteine rich nature of the protein rendered conventional protein sequencing techniques unsuitable. In this regard, WI-1 resists cleavage. It also adopts unusual configurations in stringent cleavage conditions. Thus, to date WI-1 has had to be obtained using relatively costly and time consuming isolations from natural yeast.

Thus, a need exists for a way to more quickly provide large amounts of an antigen to *B. dermatitidis* at low cost, and at consistant purity.

SUMMARY OF THE INVENTION

In one aspect the invention provides a recombinant vector containing a nucleotide sequence coding for an epitope present in SEQ ID NO:3. In another aspect, the invention provides a proteinaceous material having an epitope that is present in SEQ ID NO:3 wherein the protein has been produced by the' above nucleotide sequence.

In another aspect, one can assay for the present of *B. dermatitidis* using polymerase chain reaction techniques. One transcribes RNA from a sample to be tested to DNA. One then attempts to amplify the DNA thus formed in a polymerase chain reaction using primers homologous to portions of DNA that code for WI-1.

In yet another aspect, the antigen of the invention can be administered to a mammal to create an immune response.

It should be noted that apart from the difficulties involved in amino acid sequencing WI-1 from the protein, it has been discovered that problematic areas of secondary structure (and resistance to denaturation) prevent m-RNA from *B. dermatitidis* from being transcribed to yield other than short fragments of WI-1 cDNA. However, out of this failure came the surprising discovery that a short fragment of cDNA for WI-1 can be isolated that codes for an excellent antigen.

The objects of the invention therefore include:

(a) providing a recombinant vector with a nucleotide sequence that codes for the expression of an antigen of *B. dermatitidis;*

(b) providing improved assays for *B. dermatitidis* that either use such an antigen (or use the knowledge gained from the nucleotide sequence coding for it) to create the assay;

(c) providing highly specific, sensitive, and low cost diagnostic tests for *B. dermatitidis;* and (d) providing a means to inhibit development of *B. dermatitidis.*

These and still other objects and advantages of the present invention will be apparent from the description which follows. These embodiments do not represent the full scope of the invention. Rather, the invention may be employed in other embodiments. Reference should therefore made to the claims herein for interpreting the scope of the present invention.

GENERAL OVERVIEW

WI-1 is a 120 kD glycoprotein antigen that is expressed on *Blastomyces dematitidis* yeasts. See U.S. Pat. No. 5,093,118. We took the total RNA of the yeast, isolated the m-RNA, created DNA fragments therefrom, cloned the framents, and then screened the library to identify clones that encoded WI-1. Unfortunately, we were unable to find a clone expressing the full (or even a majority of) the protein. However, a 942 bp cDNA was isolated by immunologic screening with polyclonal, rabbit anti-WI-1 antiserum and various hybridation techniques. DNA and deduced protein sequence analysis of the clone demonstrated a 25-amino acid repeat arrayed in tandem, present in at least 4.5 copies near the 5′ end, which is highly antigenic.

The cloned cDNA was used to express a 30 kD fusion protein that was strongly recognized in western blots by rabbit anti-WI-1 antiserum, and by sera from all 35 blastomycosis patients studied. The fusion protein product of subcloned cDNA encoding only the tandem repeat also was strongly recognized in western blots by sera from the 35 blastomycosis patients, but not by sera from 10 histoplasmosis and 5 coccidioidomycosis patients. Thus, the tandem repeat encodes a highly antigenic, and highly specific antigen.

METHODS

Fungi

American Type Culture Collection (ATCC) Strains 60636 and 26199 were used for these studies. These represent virulent isolates that have been associated with human disease. Stock cultures were maintained in the yeast form on 7H10 agar enriched with oleic acidalbumin complex (Sigma Chemical Co., St. Louis, Mo.) at 37° C. Yeasts were grown in Erlenmeyer flasks containing brain heart infusion (BHI) broth (Difco Laboratories, Detroit, Mich.) at 37° C. in a gyrator shaker at 120 rpm for 72 hours. Cells were harvested by filtration through a sintered glass filter and washed with saline.

Extraction of RNA and synthesis of cDNA

Total RNA was extracted from freshly grown *B. dermatitidis* yeasts using a phenol-chloroform technique. See generally W. Fonzi et al., 5 Mol. Cell. Biol. 161-66 (1985). Diethylpyrocarbonate (DEPC)-treated water and RNAse-free glassware and plasticware were used for extracting, purifying and analyzing RNA. A 10-gm wet-weight pellet of yeasts was suspended in 10 ml lysis buffer (0.1M Tris, 0.1M lithium chloride, 0.01M dithiothreitol, pH 7.0). The cell suspension was transferred to a pre-chilled metal cannister containing 10 ml 0.45-0.50 mm glass beads, 15 ml phenol-chloroform-isoamyl alcohol (24:24:1), and 2 ml 10% SDS. The cannister was placed into a Braun model MSK homogenizer fitted with a carbon dioxide cooling device and agitated at 2,000 strokes/min for 30 second intervals before cooling. Nearly complete disruption of cells was accomplished after five intervals. The chilled mixture was centrifuged at 5,000 g for 15 min at 4° C. The aqueous layer of each tube was extracted twice with phenol and then repeatedly with phenol-chloroform-isoamyl alcohol to clear the interface of precipitate. One-tenth volume 3M sodium acetate (pH 7.0), and 2.5 volumes cold 100% ethanol were added to the aqueous layer after it was removed. Precipitated nucleic acid was centrifuged at 7500 g for 30 min at 4° C. Pellets were rinsed with 70% ethanol, dried, and diluted and stored in DEPC-treated water at −70° C.

Poly (A)+ mRNA was isolated from whole cell RNA with oligo (dT) cellulose affinity columns (Boehringer Mannheim Biochemicals, Indianapolis, Ind.). See generally J. Badley et al., 6 Biotechniques 114-116 (1988). Composition of whole cell RNA and poly (A)+ mRNA preparations was followed by agarose gel electrophoresis and $OD_{260:280}$ was used to estimate RNA concentration and purity.

Starting with 5 μg poly (A)+ RNA from strain 60636, first- and second-strand cDNA were synthesized using murine maloney leukemia virus reverse-transcriptase, oiligo (dT) primer, and other reagents and methods specified in a commercial synthesis kit (Pharmacia, Piscataway, N.J.). The ends of double-stranded cDNA were filled in with Klenow fragment and ligated to Eco R1/Not I adaptors (SEQ ID NO:1). Sephacryl S-400 spun columns (Pharmacia) were used to purify cDNA fragments larger than 400 base pairs. Each aliquot of cDNA was litigated into 100 ng of a dephosphorylated phagemid vector, pBluescript II (KS+) (Strategene, LaJolla, Calif.), which contains transcriptional and translational start sequences from the lac Z gene. After litigation, cDNA was electroporated into competent *Escherichia coli* XL1-Blue (Stratagene). See generally J. Dower et al, 16 Nuc. Acids. Res. 6127-45 (1988) (Biorad laboratory). Transformed *E. coli* were plated on LB agar containing 50 μg/ml ampicillin (Sigma), supplemented with 5 mMIPTG and 200 μg/ml X-gal (Sigma), to assess both the number of transformants and recombinants. When screening the expression library, X-gal was omitted from growth medium.

Screening the cDNA expression library with antibody and colony hybridization Transformed *E. coli* were plated on LB agar in 150-mm-diameter petri plates (Falcon, Cockeysville, Md.). After overnight growth at 37° C., bacteria were replica plated onto a fresh agar plate, and onto a 150-mm nitrocellulose sheet (Schleicher & Schuell, Keene, N.H.). After colonies grew to 1-2 mm on nitrocellulose, the filter was transferred to a fresh LB agar plate supplemented with 5 mM IPTG and incubated for an additional 2-4 hours. Bacteria on the filters were lysed and the filters processed for immunoscreening. See generally, T. Maniatis, *Molecular Cloning* (Cold Spring Harbor (1989)). Rabbit antiserum specific for WI-1 (anti-WI-1 titer, 1:10,240, as measured by radioimmunoassy [B. Klein et al. 85 J. Clin Invest 152-161 (1990)]) was used to screen a portion of the expression library. The serum was preabsorbed with *E. coli* lysate (Promega, Madison, Wis.) overnight at 4° C. Preabsorbed antiserum diluted 1:2,000 could discriminate 50 ng WI-1 spotted onto nitrocellulose from background staining of lysed *E. coli* proteins on the filter. Immunoscreening was performed with this antiserum. See generally Maniatis sucra.. Rabbit anti-WI-1 bound to nitrocellulose was detected with goat anti-rabbit immunoglobulin G conjugated with alkaline phosphatase (Promega). Positive colonies were isolated from original replica plates, replated, and rescreened with antibody until they were purified.

A WI-1-cDNA fragment identified through immunoscreening was removed from the vector by digestion with Not I (Bethesda Research Lavatory, Gaithersberg, Md.), and purified from low melting point agarose (Bethesda Research Laboratory) using Geneclean (Bio 101, Lajolla, Calif.). A 100 ng aliquot of the fragment was radiolabeled with [$\alpha$-$^{32}$P] dCTP to a specific activity of approximately $10^9$ cpm/μg using random oligonucleotides as primers (IBI, New Haven, Conn.).

Colony hybridization was performed (generally as described in Maniatis) with minor modifications in order to try to "fish" out a longer (or hopefully the full) fragment. Bacteria were transformed, cultured, and replica plated as with immunoscreening. When colonies grew to 0.1-0.2 mm on nitrocellulose, the filters were processed to lyse bacterial colonies and baked for one hour at 80° C. Bacterial debris on filters was removed by washing briefly in 5x SSC (1x SSC=150 mM NaCl, 15 mM sodium citrate). Filters were incubated in crystallizing dishes with hybridization solution containing 6x SSC, 5x Denhardts, 20 mM $Na_2PO_4$, 0.1 mg/ml polyadenylic acid. Dishes were agitated for 1 hour at 65° C. Radiolabeled probe was heat denatured by boiling for 5 minutes and placed on ice before it was added to the hybridization solution (50,000 cpm/ml). After overnight hybridization at 65° C., filters were washed free of excess probe with 1x SSC, 0.05% SDS for 15 minutes at room temperature. Dried filters were wrapped in cellophane and placed in cassettes containing intensifying screens and X-Omat AR film (Eastman Kodak, Rochester, N.Y.). Autoradiographs were developed after incubating cassettes for 2 to 72 hours at −80° C. Positive colonies were isolated from original replica plates, replated, and rescreened with probe until they were purified.

Northern hybridizations

To try to learn more about the length of the full WI-1 m-RNA (given the apparent inability to obtain a long cDNA), total RNA samples of (20 μg) were electrophoresed through 1% agarose gels in MOPS/2.2 M formaldehyde for 16–18 hours at 30 volts and transferred by capillary action to Nytran (Schleiller and Schuell) membranes using 10x SSC. DNA fragments for hybridization were radioactively labelled with [α-$^{32}$P] d CTP using random oligonucleotides as primers (IBI). The WI-1 cDNA probe was obtained as described for colony hybridization above. An actin DNA probe from *Histoplasma capsulatum* was the generous gift of E. Keith and was used to assess loading variation. RNA molecular weight markers were purchased from BRL-Gibco. Probes were hybridized to filters in 40% formamide for high stringency or 20% formamide for low stringency, 0.25M Na+($PO_4$), 1 mM EDTA, 7% SDS at 42° C. for 16–24 hours. Hybridized filters were washed first in 2x SSC at room temperature for 2–5 minutes, then in 0.25M Na+($PO_4$), 1 mM EDTA, 2% SDS at 64° C. for high stringency or 55° C. for low stringency twice for 10 minutes, next in 0.04M Na+($PO_4$), 1 mM EDTA, 1% SDS at 64° C. for high stringency or 55° C. for low stringency once for 40–60 minutes, and finally rinsed in 4x SSC at room temperature. See generally D. Holden, et al., 8 EMBO J 1927–34 (1989). Washed blots were used to expose Kodak XAR-5 film with intensifying screens at −80° C.

Sequence analysis

Single-stranded and double-stranded plasmid sequencing was performed according to the protocols supplied using a Sequence 2.0 polymerase kit (USBiochemicals, Cleveland, Ohio). Single-stranded DNA was prepared from pKS+ phagemid clones by standard methods (See Maniatis, supra). Sequence primers homologous to the pKS+vector polylinker were the T3 and SK primers (USBiochemicals). Three sets of primers homologous to internal sequences in the cDNA insert were purchased from Operon Technologies (Alameda, Calif.). The complete sequence of both strands was determined.

Expression and immunologic assessment of fusion protein

Transformed E. coli bearing the gene of interest was grown in LB media containing 50 μg/ml ampicillin and 12.5 μg/ml tetracycline in a gyrator shaker at 37° C. When the density of the culture reached $OD_{600}$=0.6 (after about four hours of growth), 5 mM IPTG was added. Optimal lac Z gene expression and production of the fusion protein was examined at one hour intervals after induction. Bacteria were centrifuged at 5,000 g for 15 min at 4° C. A lysate was prepared by resuspending the pellet in 1x gel loading buffer (50 mM Tris, pH 6.8, 100 mM dithiothreitol, 2% SDS, 0.1% bromphenol blue, 10% glycerol) equivalent to 0.1 volume of the original culture. The lysate was heated to 100° C. for 3 minutes and centrifuged at 12,000 g for 1 minute at room temperature.

Lysates of *E. coli* containing vector alone to be used as antigen inhibitors of antibody binding in radioimmunoassays (RIAs) were prepared without reducing agents. Bacteria were resuspended 1:4 (w/v) in a lysis buffer (50 mM Tris, pH 8.0, 1 mM EDTA, 100 μM PMSF, and 10% sucrose) to which lysozyme (1 mg/ml) and Triton x-100 (0.1%) were added before centrifugation at 12,000 g for 30 min. Lysates were examined by SDS-polyacrylamide gel. Gels were stained for protein with Coomassie brilliant blue.

RIA TEST USING THE ANTIGEN

To assess antibody recognition of the fusion protein, western blots of gels were prepared. See generally H. Towbin et al., 76 P.N.A.S. USA 4350–4354 (1979). Human antisera used in these experiments were from blastomycosis patients in whom antibody responses to WI-1 had previously been demonstrated by RIA and from seronegative control subjects with other fungal diseases or no illness. Sera had been stored at −70° C. for up to 8 years prior to testing.

The fusion protein was electroeluted from polyacrylamide gels (B. Klein, et al., supra) for further immunologic studies. To determine the relative importance of immunologic determinants on the fusion protein, an antigen-inhibition RIA was used. It examined the ability of samples of eluted protein or crude *E. coli* lysate to block anti-WI-1 antibody binding to radiolabeled WI-1. Briefly, RIAs were constructed using 0.1–5 ng radiolabeled WI-1 as a target. Assays were done in 12 ×75 mm acid-washed glass tubes. We used 0.1% BSA in 0.04M Na phosphate, 0.15M NaCl, pH 7.5 (BSA-PBS) as a carrier solution.

A test sample consisted of 0.1 ml of diluted serum and 0.1 ml of radiolabeled antigen. When an antigen-inhibition RIA was done, 0.1 ml of the inhibitor or BSA-PBS was added to diluted antibody in appropriate tubes. All tubes were incubated 4–18 hrs at 4° C. before radiolabeled antigen was added. For each antigen-inhibition RIA performed, a preliminary RIA was done to determine the dilution of serum which bound approximately 50% of radiolabeled antigen target. This dilution of serum was added to tubes of the antigen-inhibition RIA. For RIAs and antigen-inhibition RIAs, 2 mg insoluble staphlococcal protein A (Sigma) was added to each sample and control tube after overnight incubation at 4° C. Precipitates were centrifuged at 2000 g for 10–40 min and a volume of supernatant was removed from each tube for counting in a gamma counter. We corrected for coprecipitation in RIAs. See P. Minden et al., Handbook Of Experimental Immunology, p 463–492 (1967).

RESULTS

A 20 gm wet-weight pellet of B. dermatitidis yeasts strain ATCC 60636 yielded 50 mg total RNA with $OD_{260:280}$ ratio of 2.17. Affinity purification of 10 mg total RNA yielded approximately 100 μg poly (A)+ mRNA. Agarose gel electropheresis of total RNA showed abundant and distinct 28S and 18S ribosomal bands. Poly (A)+ mRNA showed little remaining ribosomal RNA and a size range up to approximately 14 kB.

Identification of WI-1 cDNA clones

Approximately $10^6$ recombinants were obtained in the expression library. Rabbit anti-WI-1 antibody was used to screen 2000 recombinants and identified two positive clones. The cDNA inserts in plasmids from these clones were estimated to be approximately 700 bp and 950 bp by Not I digestion of the plasmids; Eco R1 digestion yielded a common fragment by approximately 430 bp. Colony hybridization was used to screen an additional 10,000 recombinants and identified an additional 25 independent, positive clones. Not I digestion demonstrated each cDNA to be approximately 950 bp and contain the common enzyme restriction site for Eco RI.

Northern hybridizations using WI-1 cDNA to probe *B. dermatitidis* RNA illustrates that the full length message for WI-1 is approximately 3.9 kB (FIG. 1). WI-1 message is abundantly expressed in the yeast strain 60636, from which the partial cDNA was cloned, as well as in the unrelated strain 26199.

WI-1 cDNA sequence

DNA sequence analysis of the largest clone isolated by immunoscreening is shown as SEQ ID NO:2. The 942 bp sequence contains two open reading frames. One open reading frame predicts an amino acid sequence conforming very closely with the relative amino acid composition of WI-1. The predicted molecular mass of the recombinant antigen is 25.5 kD; 3.5 kD encoded by plasmid $\beta$-galactosidase fusion sequences and the remainder by the WI-1 insert. The DNA sequence predicts an amino acid sequence SEQ ID NO:3 that has within it a 25-amino acid repeat (e.g. DNA 130–225) arrayed in tandem, present in 4.5 copies near the 5′ end, with amino acid variations in only two positions (serine versus tyrosine, residues 3,28,53,78,103; and serine for asparagine, residue 113).

Expression of the fusion protein

Lysates of *E. coli* XL1-blue transformed with the pBluescript II vector alone or the vector plus 942 bp WI-1 insert, studied by SDS-PAGE, show that a fusion protein of approximately 30 kD is expressed by 2 hours and produced maximally by 4 hours after induction with IPTG. This protein may represent WI-1 cleaved from the 3.5 kD $\beta$-galactosidase fusion partner, since the same lysate also contains smaller amounts of 33.5 kD protein that is enriched in comparison to control lysates. Rabbit anti-WI-1 specifically recognizes both of these proteins in a western blot.

Human immune responses to WI-1 fusion proteins

Forty-six sera from 35 patients with culture-confirmed cases of blastomycosis were tested for recognition of proteins in the *E. coli* lysates. Nineteen (54%) of the patients had isolated pulmonary disease, the remainder had disseminated disease involving skin alone (8 patients); lung and skin (5); lung, skin, and brain (1); brain alone (1); and eye alone (1). Titers of antibody to WI-1 in these patients ranged from 1:100 to 1:34,000 (geometric mean titer, 1:850). All sera tested reacted specifically with WI-1 fusion protein in western blots. Preabsorption of rabbit and human anti-WI-1 antisera with either the eluted fusion protein or with *E. coli* lysate containing the fusion protein nearly eliminated recognition of radiolabeled WI-1 in the RIA, whereas preabsorption with *E. coli* lysate without the fusion protein had no influence on WI-1 recognition. The fusion protein further inhibited anti-WI-1 binding to $^{125}$I-WI-1 in a dose-dependent manner (FIG. 7C), with 2 $\mu$g protein inhibiting 100% of binding by either rabbit or human antiserum.

Subcloning and immunologic study of the tandem repeat

We examined whether the tandem repeat of cloned WI-1 cDNA was an important site for anti-WI-1 antibody recognition. Restriction sites bounding the repeats were used to subclone a 372 bp fragment encoding 4.5 copies of the tandem repeat into pBluescript II. A Fok 1 digest of WI-1 cDNA yielded a 1678 bp fragment including the tandem repeats plus five additional bases at the 3′ end and a portion of vector at the 5′ end. After the ends were made blunt with Klenow treatment, a Hind III digest, which cuts in the polylinker site of pBluescript, was used to separate the cDNA and vector. The 372 bp fragment was purified and cloned directionally into pBluescript II cut with Hind III and Sma I. Ligated cDNA was electroporated into *E. coli* XL-1 Blue and the transformants were assessed for recombinants by blue/white color selection. Fusion protein encoded by subcloned cDNA was expressed in *E. coli* as above. When studied by SDS-PAGE, the fusion protein comprised by tandem repeats is produced maximally by 4 hrs after induction with IPTG, migrates at approximately 21 kD, and is recognized specifically by rabbit anti-WI-1 antiserum in a western blot.

Sera from the 35 blastomycosis patients studied above were examined for recognition of the tandem repeat by western blot. All of them reacted with the protein, whereas none of the sera from ten patients with histoplasmosis (complement fixation titers, 1:32 to 1:512; median titer, 1:128) or five patients with coccidioidomycosis (complement fixation titers, 1:32 to 1:64; median titer, 1:64) reacted.

To assess the relative importance of the tandem repeat in antibody recognition of WI-1, we tested the 21 kD fusion protein in the antigen-inhibition RIA using anti-WI-1 antisera from ten blastomycosis patients and an immunized rabbit. The tandem repeat inhibited a mean of 96% (range 85% to 100%) of the antibody binding to radiolabeled WI-1 in the blastomycosis patients, and 87% of the binding of antibody in the immune rabbit.

PRODUCTION OF ANTIGEN

Restriction sites bounding the repeats were used to subclone a 372 bp fragment encoding 4.5 copies of the tandem repeat into pBluescript II (Stratagene, LaJolla, Calif.). A Fok 1 digest of WI-1 cDNA yielded a 1678 bp fragment including the tandem repeats plus five additional bases at the 3′ end and a portion of vector at the 5′ end. After the ends were made blunt with Klenow treatment, a Hind III digest, which cuts in the polylinker site of pBluescript, was used to separate the cDNA and vector. The 372 bp fragment was purified and cloned directionally into pBluescript II cut into *E. Coli* XL-1 Blue (Stratagene) and the transformants were assessed for recombinants by blue/white color selection.

Fusion protein encoded by subcloned cDNA was expressed in *E. coli* as above. When studied by SDS-PAGE, the fusion protein comprised by tandem repeats is produced maximally by 4 hrs after induction with IPTG, migrates at approximately 21 kD, and is recognized specifically by rabbit anti-WI-1 antiserum in a Western blot.

In the alternative, one can subclone the cDNA fragment encoding the tandem repeat into plasmid vector pQE (Qiagen). It offers a system for producing and purifying large amounts of recombinant protein. This system links the recombinant protein to a six histidine residue tail. These residues have a very high affinity for nickel and the interaction of histidine-tagged protein with a nickel agarose column has permitted rapid purification of large amounts of the recombinant protein. A protocol describing the approach appears in Protocol

#7, page 45, of the QIA Express Instruction Manual (1992).

USE OF ANTIGEN

A preferred RIA involves labelling the antigen with radioactive iodine, mixing the labelled WI-1 with the serum, adding a precipitating compound (e.g. Staphylococcal Protein A) that will cause protein bound to antibody to precipitate out, separating the precipitated material from the liquid, measuring the radioactivity of either the precipitate or the liquid, and comparing the results to controls. The antigen can be labelled with $^{125}I$ using N-chlorobenzenesulfonamide as an oxidizing agent. See J. Jones, 30 Infect. Immun. 78-89 (1980). By adjusting labelling conditions, one could vary the specific radioactivity of [$^{125}I$] WI-1 between 2,000 and 10,000 cpm/ng.

One can use 1% BSA in 0.04M $NaH_2PO_4$, 0.15M NaCl, pH 7.5 (PBS) as the carrier solution in the RIA. All sera being tested can be diluted serially in BSA-PBS in flat-bottom, 96-well microtiter plates (Costar, Cambridge, Mass.). Dilutions of 1:40 and greater can be tested. Each experimental or control serum sample can be analyzed in duplicate. A test sample can consist of 0.1 ml of diluted serum and 0.1 ml of BSA-PBS containing 5 ng of [$^{125}I$] WI-1. Coprecipitation controls for antibody measurements can contain 0.1 ml of BSA-PBS in place of diluted test serum. After incubating for 1 hour at 37° C. and overnight at 4° C, 1 mg of the Staphylococcal Protein A (Sigma) in 0.2 ml of PBS can be added to each sample. Precipitates can be centrifuged at 2,000 x g or 10 minutes at room temperature and 0.2 ml of each supernatant can be counted in a gamma counter.

Coprecipitation can be corrected for in all RIAs by the method of P. Minden et al., Handbook Of Experimental Immunology 463-492 (1967). The dilution of each latest serum that specifically bound 20% of the labelled antigen dose can be calculated by linear regression analysis. J. Jones, 30 Infect. Immun. 78-89 (1980), using the data points of the three dilutions that have binding values closest to 20%. A standard lot or rabbit antiserum derived by immunizing the animal with unlabelled WI-1 can be assayed with each run of experimental sera titered for antibody to the labelled antigen. This insures that there is no significant run-to-run variation in the sensitivity of the assay. See also B. Klein et al., 85 J. Clin. Invest. 152-161 (1990) (RIA using cell extracted WI-1).

Various other assays can be designed based on the antigen. For example, the antigen can be bound to a well (the well then being the "label"). Serum can then be washed over the well and various known anti-antibody systems can be used to identify the level of WI-1 antibody bound to the wells. ELISA or other techniques can also be used.

PCR ASSAY

As noted in J. Donofrio et al., PCR Methods And Applications 263-268 (1992) (Cold Spring Harbor), once one knows a unique cDNA for a substance one can form an assay using PCR techniques. In the present cause, one would create unique primers of at least 20 bases in length homologous to sites in SEQ ID NO:2. For example, primers might be homologous to nucleotides 359-378 and 468-487. Using the primers, PCR is then run on DNA made from the RNA of unknowns. If DNA appears, the disease is present.

An example protocol is:

(a) Synthesize primers by the β-cyanoethyl phosphoramidite method.

(b) In a sterile microfuge tube, mix in the following order
 30 μl sterile $H_2O$
 10 μl 10x Amplification Buffer
 16 μl mixture of 4 dNTPs, each at 2 mM
 50 pmoles primer 1
 50 pmoles primer 2
 100 ng template DNA
 $H_2O$ to a final volume of 100 μl 10x Amplification Buffer consists of:
 500 mM KCl
 100 mM (Tris-Cl) pH 8.3
 X mM Mg C12 *
 0.1% gelatin

*The optimal $MgCl_2$ concentration varies from 0.5-10 mM and should be optimized for each primer pair.

(c) Heat the reaction mixture for 5 minutes at 94° C.

(d) While the mixture is still at 94° C., add 2.5 units Taq DNA polymerase.

(e) Overlay the reaction mixture with 100 μl of light mineral oil.

(f) Perform the PCR amplification reactions in an automated thermal cycler set to the following parameters:

| | |
|---|---|
| Cycle 1 (1 time) | 5 minutes at 94° C. |
| | 2 minutes at 59° C. |
| | 1 minute at 73° C. |
| Cycle 2 (25-30 times) | 1.5 minutes at 94° C. |
| | 2 minutes at 59° C. |
| | 1 minute at 73° C. |
| Final Cycle (1 time) | 1.5 minutes at 94° C. |
| | 2 minutes at 59° C. |
| | 10 minutes at 73° C. |

(g) A sample of the reaction mixture is then withdrawn and analyzed by gel electrophoresis.

(h) Using the primers specified in the example, a DNA product of 128 base pairs should be produced if the specimen (e.g. unknown) has the DNA. This product can be digested with the restriction enzyme Fok I yielding products of 51 base pairs and 77 base pairs. DNA fragments in this size range can be detected after electrophoresis through a 6% acrylamide gel and staining with Ethidium bromide for visualization under UV.

VACCINE

The preferred 25 amino acid antigen has been found to elicit an unusually strong antigenic reaction. One can therefore deliver the antigen (e.g. by injection) to a dog or other host in non-toxic and effective amounts. The injections (or other administration) would be repeated until an immune response occurs. As an example, 10 μg (or other amounts) of protein could be given in 0.1 ml sterile deionized, distilled water. Subcutaneous injections would be administered weekly for 4 weeks (or other periods) in complete Freund adjuvant, and then biweekly in incomplete Freund adjuvant for 8 weeks (or other periods).

It will be appreciated that the above describes only the preferred embodiments of the invention. A number of other modifications and changes are within the scope of the invention and are intended to be included within the scope of the claims. The claims should therefore be looked to in judging the scope of the invention.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: nucleotide ( i i i ) HYPOTHETICAL: NO ( i v ) ANTI-SENSE: NO ( v i ) ORIGINAL SOURCE:

( x i ) SEQUENCE DESCRIPTION: SEQ ID NO:1:

AATTCGGGGC CGC 13

( 2 ) INFORMATION FOR SEQ ID NO:2:

( i ) SEQUENCE CHARACTERISTICS:
( A ) LENGTH: 942 base pairs
( B ) TYPE: nucleic acid
( C ) STRANDEDNESS: double
( D ) TOPOLOGY: linear ( i i ) MOLECULE TYPE: oligonucleotide ( i i i ) HYPOTHETICAL: NO ( i v ) ANTI-SENSE: NO ( v i ) ORIGINAL SOURCE: B. Dermatitidis ( x i ) SEQUENCE DESCRIPTION: SEQ ID NO:2:

GGATCCATAT CATGAGAAGT ATGATTGGGA TCTCTGGAAT AAGTGGTGCA ACAAGGACCC 60
CTACAACTGC GACTGGGACC CATCTCATGA GAAGTATGAT TGGGATCTCT GGAATAAGTG 120
GTGCAACAAG GACCCCTACA ACTGTGACTG GGACCCATAT CATGAGAAGT ATGATTGGGA 180
TCTCTGGAAT AAGTGGTGCA ACAAGGACCC CTACAACTGT GACTGGGACC CATATCATGA 240
GAAGTATGAT TGGGATCTCT GGAATAAGTG GTGCAACAAG GACCCCTACA ACTGTGACTG 300
GGACCCATCT CATGAGAAGT ACGATTGGGA TCTCTGGAGT AAGTGGTGCA ACAAGCACGA 360
CGAGCACGAC AAACATCCAT TGTGCCCTGT CTGTGACCCC CTCTCAGGCA AAAATCACTG 420
TCATCCAACC ACTTCCTGTG TCAGCACAGG CCACCACTAC CACTGCGCCT GCCGCGCTGG 480
CTACAAGGCT AGCCATTATA GCCATGACCA CAAGCATTTC CGCATGCCAG TCAAAGGCTA 540
TGAATTCCTT GTTTTCACCG GCCCGCATAC CAAGTGCAAT GTCCTTTGCG ACGGTTACCC 600
GCACAAGCCA GCCCATGAGC TTTGCGGCGA GGTTAAGGTT CATAATTATT GCGGGCCATG 660
AGCTTCCTTT GAGGGAAAGC GCAGAAAGAG GGAAATTTGG GGTGATTTTG GAGTACTTGA 720
ACAGATTTAT TTTCCTCGTT TTGAGGGAGG GAGAAAGCGA ACATGTAATT TTGTAGATGG 780
GTGGAAAGCT TCATCTGACC TCTGGACGAG GTCATTTTTT CCCTTTTATT ATGGATAAAT 840
ATTGATGAAG TTGGATAATA GGGAGACATC TTTTTGCAAA ATTAATAGTT ATATATATGA 900
GTTAGATTAC CTTCTTAATT AGATGCTTTA ATGATTTTTG TG 942

-continued ( 2 ) INFORMATION FOR SEQ ID NO:3:

( i ) SEQUENCE CHARACTERISTICS:
( A ) LENGTH: 118 amino acids
( B ) TYPE: amino acid
( C ) TOPOLOGY: linear ( i i ) MOLECULE TYPE: protein ( i i i ) HYPOTHETICAL: NO ( i v ) ANTI-SENSE: NO ( v i ) ORIGINAL SOURCE: B. Dermatitidis ( x i ) SEQUENCE DESCRIPTION: SEQ ID NO:3:

Asp Pro Tyr His Glu Lys Tyr Asp Trp Asp Leu Trp Asn Lys Trp Cys Asn
5 10 15

Lys Asp Pro Tyr Asn Cys Asp Trp Asp Pro Ser His Glu Lys Tyr Asp Trp
20 25 30

Asp Leu Trp Asn Lys Trp Cys Asn Lys Asp Pro Tyr Asn Cys Asp Trp Asp
35 40 45 50

Pro Tyr His Glu Lys Tyr Asp Trp Asp Leu Trp Asn Lys Trp Cys Asn Lys
55 60 65

Asp Pro Tyr Asn Cys Asp Trp Asp Pro Tyr His Glu Lys Tyr Asp Trp Asp
70 75 80 85

Leu Trp Asn Lys Trp Cys Asn Lys Asp Pro Tyr Asn Cys Asp Trp Asp Pro
90 95 100

Ser His Glu Lys Tyr Asp Trp Asp Leu Trp Ser Lys Trp Cys Asn Lys
105 110 115

We claim:

1. A recombinant vector containing a cDNA having a nucleotide sequence which codes for a twenty-five amino acid residue epitope portion of a WI-1 protein, said nucleotide sequence being selected from the group consisting of residues 1-25 of SEQ ID NO: 3, residues 26-50 of SEQ ID NO: 3, residues 51-75 of SEQ ID NO: 3, and residues 76-100 of SEQ ID NO: 3.

* * * * *

UNITED STATES PATENT AND TRADEMARK OFFICE
CERTIFICATE OF CORRECTION

PATENT NO. : 5,302,530

DATED : April 12, 1994

INVENTOR(S) : Bruce S. Klein, *et al*.

It is certified that error appears in the above-identified patent and that said Letters Patent is hereby corrected as shown below:

| | |
|---|---|
| Column 8, line 48 | after "cut" add: with Hind III and Sma I. Ligated cDNA was electroplated |
| Columns 13 and 14 SEQ ID NO:3 | The numbering should start with the first residue being 1, not 5. Thus, SEQ ID NO:3 should appear as per attached page. |

Signed and Sealed this

Ninth Day of August, 1994

Attest:

Bruce Lehman

BRUCE LEHMAN

*Attesting Officer*

*Commissioner of Patents and Trademarks*

(vi) ORIGINAL SOURCE: B. Dermatitidis (xi) SEQUENCE DESCRIPTION: SEQ ID NO:3:

| | | | | | | | | | | | | | | | | |
|---|---|---|---|---|---|---|---|---|---|---|---|---|---|---|---|---|
| Asp | Pro | Tyr | His | Glu | Lys | Tyr | Asp | Trp | Asp | Leu | Trp | Asn | Lys | Trp | Cys | Asn |
| | | | | 5 | | | | | 10 | | | | | 15 | | |
| Lys | Asp | Pro | Tyr | Asn | Cys | Asp | Trp | Asp | Pro | Ser | His | Glu | Lys | Tyr | Asp | Trp |
| | | 20 | | | | | 25 | | | | | 30 | | | | |
| Asp | Leu | Trp | Asn | Lys | Trp | Cys | Asn | Lys | Asp | Pro | Tyr | Asn | Cys | Asp | Trp | Asp |
| 35 | | | | | 40 | | | | | 45 | | | | | 50 | |
| Pro | Tyr | His | Glu | Lys | Tyr | Asp | Trp | Asp | Leu | Trp | Asn | Lys | Trp | Cys | Asn | Lys |
| | | | 55 | | | | | 60 | | | | | 65 | | | |
| Asp | Pro | Tyr | Asn | Cys | Asp | Trp | Asp | Pro | Tyr | His | Glu | Lys | Tyr | Asp | Trp | Asp |
| | 70 | | | | | 75 | | | | | 80 | | | | | 85 |
| Leu | Trp | Asn | Lys | Trp | Cys | Asn | Lys | Asp | Pro | Tyr | Asn | Cys | Asp | Trp | Asp | Pro |
| | | | | 90 | | | | | 95 | | | | | 100 | | |
| Ser | His | Glu | Lys | Tyr | Asp | Trp | Asp | Leu | Trp | Ser | Lys | Trp | Cys | Asn | Lys | |
| | | 105 | | | | | 110 | | | | | 115 | | | | |